United States Patent [19]
Faccioli et al.

[11] Patent Number: 6,102,911
[45] Date of Patent: *Aug. 15, 2000

[54] ORTHOPAEDIC APPARATUS, PARTICULARLY FOR THE SURGICAL CORRECTION OF BONE DEFORMITIES

[75] Inventors: Giovanni Faccioli, Monzambano; Daniele Venturini, Povegliano Veronese; Sander Ten Veldhuijs, Verona, all of Italy

[73] Assignee: Orthofix S.r.l., Bussolengo Verona, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 09/023,018

[22] Filed: Feb. 11, 1998

[30] Foreign Application Priority Data

Feb. 13, 1997 [IT] Italy ................... VR97A0011

[51] Int. Cl.[7] ............................................. A61B 17/56
[52] U.S. Cl. ............................ 606/54; 606/55; 606/59; 606/96
[58] Field of Search ..................... 606/54, 55, 56, 606/57, 58, 59, 96, 97, 98

[56] References Cited

U.S. PATENT DOCUMENTS

| | | |
|---|---|---|
| 2,391,537 | 12/1945 | Anderson . |
| 4,502,473 | 3/1985 | Harris et al. . |
| 4,628,922 | 12/1986 | Dewar . |
| 4,920,959 | 5/1990 | Witzel et al. . |
| 5,152,280 | 10/1992 | Danieli . |
| 5,160,335 | 11/1992 | Wagenknecht . |
| 5,207,676 | 5/1993 | Canadell et al. . |
| 5,292,322 | 3/1994 | Faccioli et al. . |
| 5,342,360 | 8/1994 | Faccioli et al. . |
| 5,728,096 | 3/1998 | Faccioli et al. . |

FOREIGN PATENT DOCUMENTS

| | | | |
|---|---|---|---|
| 2557933 | 1/1984 | France | ............. F16B 9/02 |
| 4238582 | 5/1994 | Germany . | |
| 9111151 | 8/1990 | WIPO | ............. A61B 17/60 |
| 9605777 | 2/1996 | WIPO . | |
| 9635386 | 11/1996 | WIPO . | |

OTHER PUBLICATIONS

Orthofix Srl., "Orthofix® Modulsystem", Jul. 1997, prior edition before Feb. 11, 1997, 16 pages.

Saleh, "Orthofix® Modulsystem, Operative Technique, Limb Reconstruction System", Orthofix Srl., Mar. 1998, prior edition before Feb. 11, 1997, 67 pages.

Pfeil, "Heidelberg External Fixation, Unilateral Techniques in Limb Deformity Corrections," George Thieme Verlag, 1998 Wandrey trans. (1st ed. 1994), 48 pages.

Orthofix Srl., "Orthofix® Modulsystem," General Application Instructions, Jan. 1996, 28 pages.

European Search Report, application No. EP 97 12 2920, Mar. 17, 1999, 2 pages.

*Primary Examiner*—Michael Buiz
*Assistant Examiner*—Lien Ngo
*Attorney, Agent, or Firm*—Hopgood, Calimafde, Kalil & Judlowe, LLP

[57] ABSTRACT

An orthopaedic apparatus, particularly for the surgical correction of angular and longitudinal defects of the bones of limbs, of the femur and tibia type, comprising a longitudinal rod externally positionable substantially parallel to a bone for correction, a first clamp movably anchored to the rod for supporting drilling guides for screws insertable in a proximal portion of the bone, and at least one second clamp movably anchored to the rod for supporting drilling guides for screws insertable in a distal portion of the bone. The first and second clamps are orientable and selectively lockable, before the surgical intervention, in predetermined angular positions with respect to the rod corresponding to the angular deformations of the bone, and are repositionable with respect to the rod in correct angular positions after the osteosynthesis for the proximal and distal portions of the bone so as to eliminate the angular deformations of the bone.

22 Claims, 10 Drawing Sheets

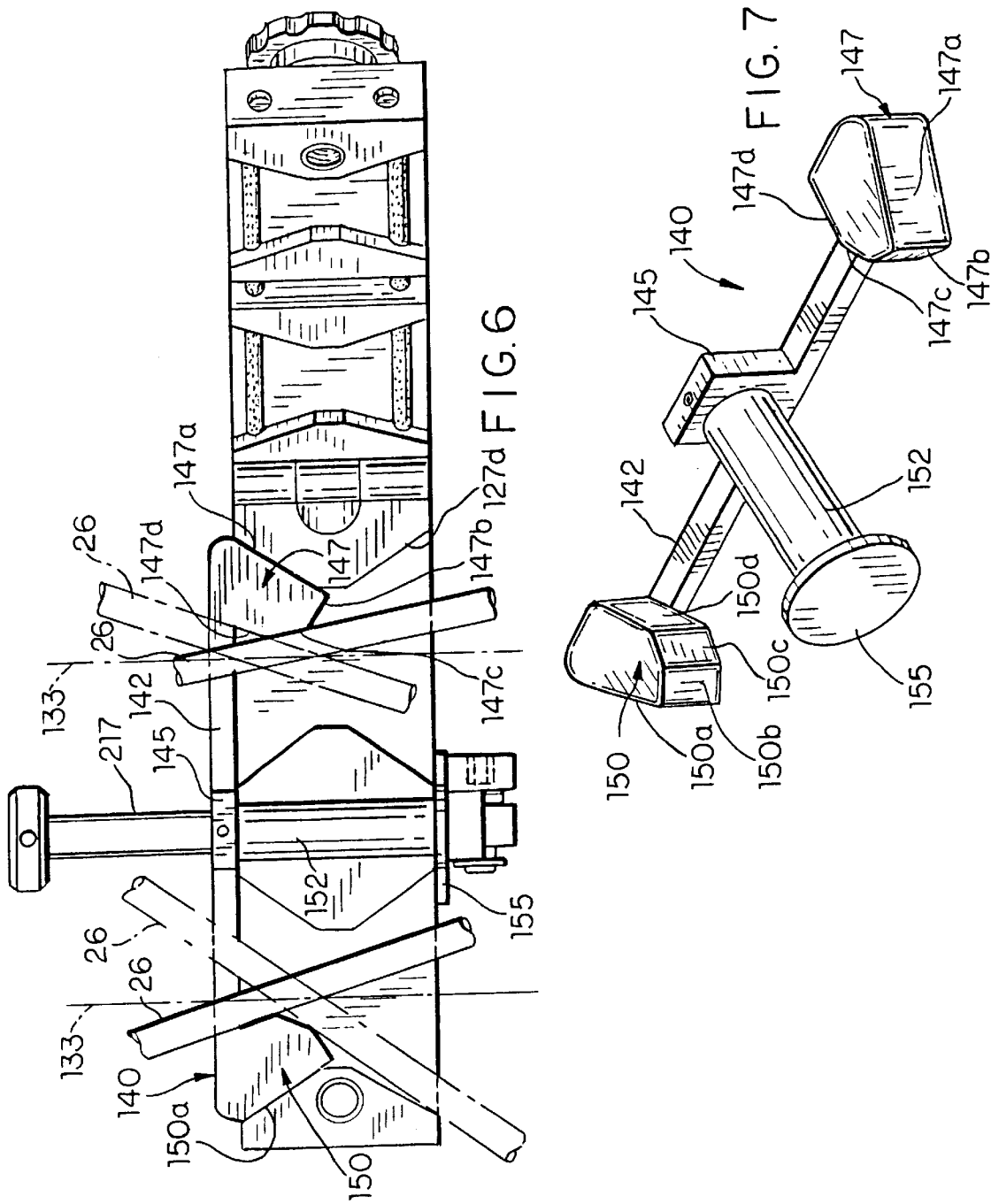

ORTHOPAEDIC APPARATUS, PARTICULARLY FOR THE SURGICAL CORRECTION OF BONE DEFORMITIES

BACKGROUND OF THE INVENTION

The present invention relates to an orthopaedic apparatus, particularly for the surgical correction of bone deformities, for example of the tibia and of the femur.

It is known that adjustable external fixation devices are commonly utilized for correcting certain angular and longitudinal deformities of long bones. Such devices essentially comprise groups of bone screws fixed in the bone portions affected by angular defects; the screws are held by clamps which are in turn slidably mounted on longitudinal guides and are thus externally positionable at the limb to be reconstructed.

The correction normally is carried out gradually with the aid of compression/distraction devices which act on the imobile clamps while the bone callous regenerates itself to produce a certain degree of corrective deformation.

This methodology, however much effective, requires correction times which are rather long and does not yield any immediate result for the patient.

BRIEF STATEMENT OF THE INVENTION

The present invention in accordance with one preferred aspect proposes to carry out an integral and immediate correction in the operating room of the defects obtained preliminarily by the surgeon by means of normal radiological procedures.

With this principal aim in mind, there is provided an orthopaedic apparatus, particularly for the surgical correction of angular and longitudinal defects (deformities) of the bones of limbs, of the femur and tibia type, which apparatus comprises a longitudinal rod externally positionable substantially parallel to a bone having a deformity to be corrected, a first clamp movably anchored to said rod for supporting drilling guides for screws insertable in a proximal portion of the bone, and at least one second clamp movably anchored to said rod for supporting drilling guides for screws insertable in a distal portion of the bone, said first and second clamps being orientable and selectively lockable, prior to surgical intervention, in predetermined angular positions with respect to said longitudinal rod corresponding to the angular deformity of the bone, and being repositionable with respect to said rod in correct angular positions after osteosynthesis of the proximal and distal portions of the bone so as to retain corrective angular deformations of the bone.

BRIEF DESCRIPTION OF THE DRAWINGS

The characteristics and advantages of the invention will become apparent from ensuing description of a preferred embodiment of the apparatus according to the invention, shown for illustrative and nonlimiting purposes, in conjunction with the attached drawings, in which:

FIG. 6 is a view taken in the direction of FIG. 5, to the scale of FIG. 5, showing the alignment bracket positioned on the base plate of the proximal bone screw clamp, the cover being in the open position;

FIG. 7 is a perspective view of the alignment bracket removed from the proximal bone screw clamp of FIG. 6, and turned upside down relative to its orientation in FIG. 2;

Corresponding reference characters indicate corresponding parts throughout the several views of the drawings.

DETAILED DESCRIPTION

Figure 1:
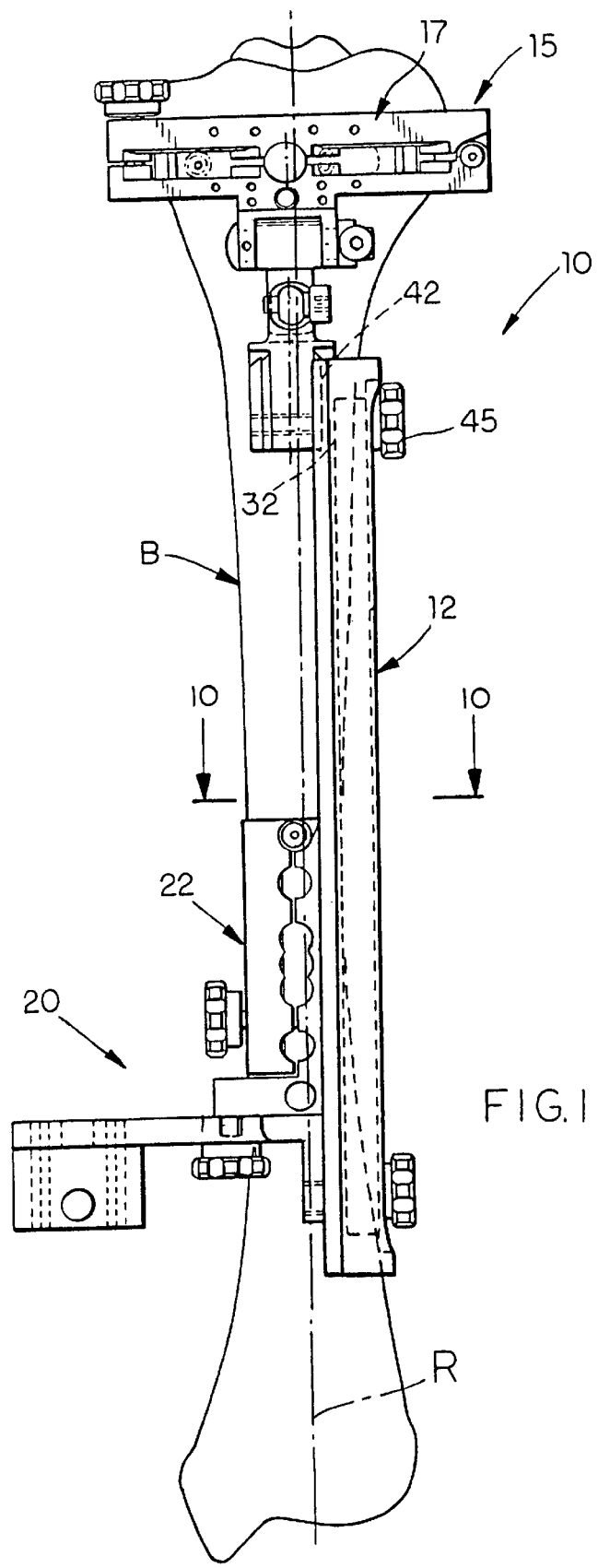
FIG. 1 is a front-elevation view of an orthopaedic apparatus or fixator according to a preferred aspect of the invention, applied to a bone after correction.

In the drawings, an orthopaedic apparatus or fixator for use in an operating room according to a preferred aspect of the invention is indicated generally by the reference numeral 10. The fixator 10 comprises essentially a longitudinal rod or guide rail 12 upon which a first or proximal clamp assembly 15, including a first or proximal bone screw clamp 17, and a second or distal clamp assembly 20, including a second or distal bone screw clamp 22, are movably mounted for supporting drill guides 25 for bone screws 26.

Figure 10:
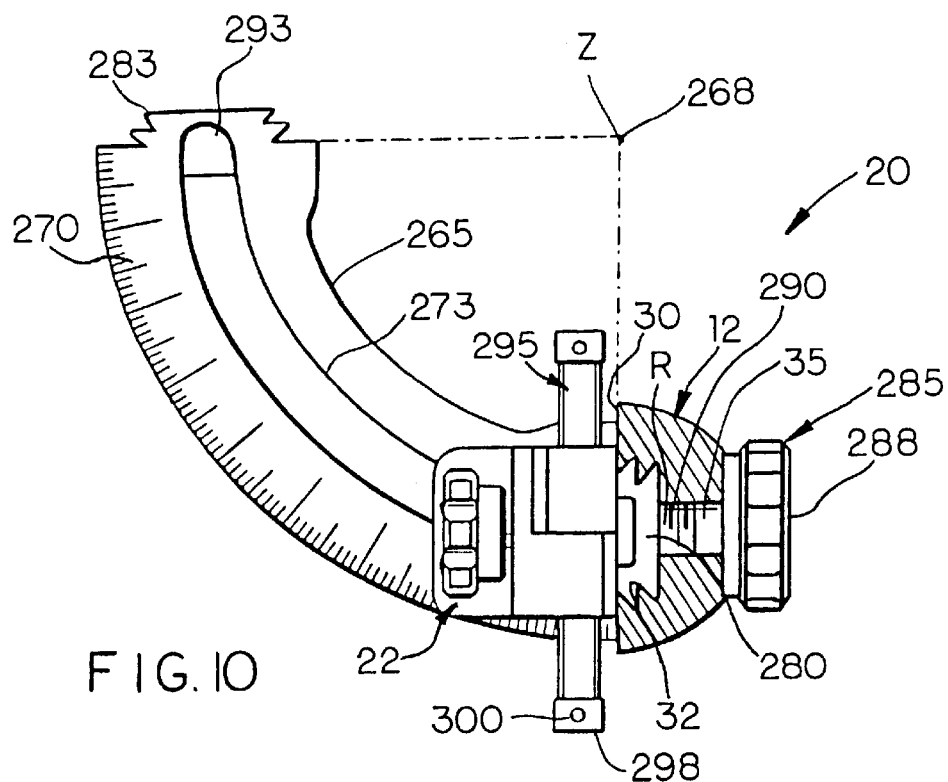
FIG. 10 is a sectional view of FIG. 1 taken in the plane 10—10 of FIG. 1, showing the second or distal clamp assembly of the apparatus of FIG. 1, in the enlarged-scale detail of FIG. 2.
Figure 12:
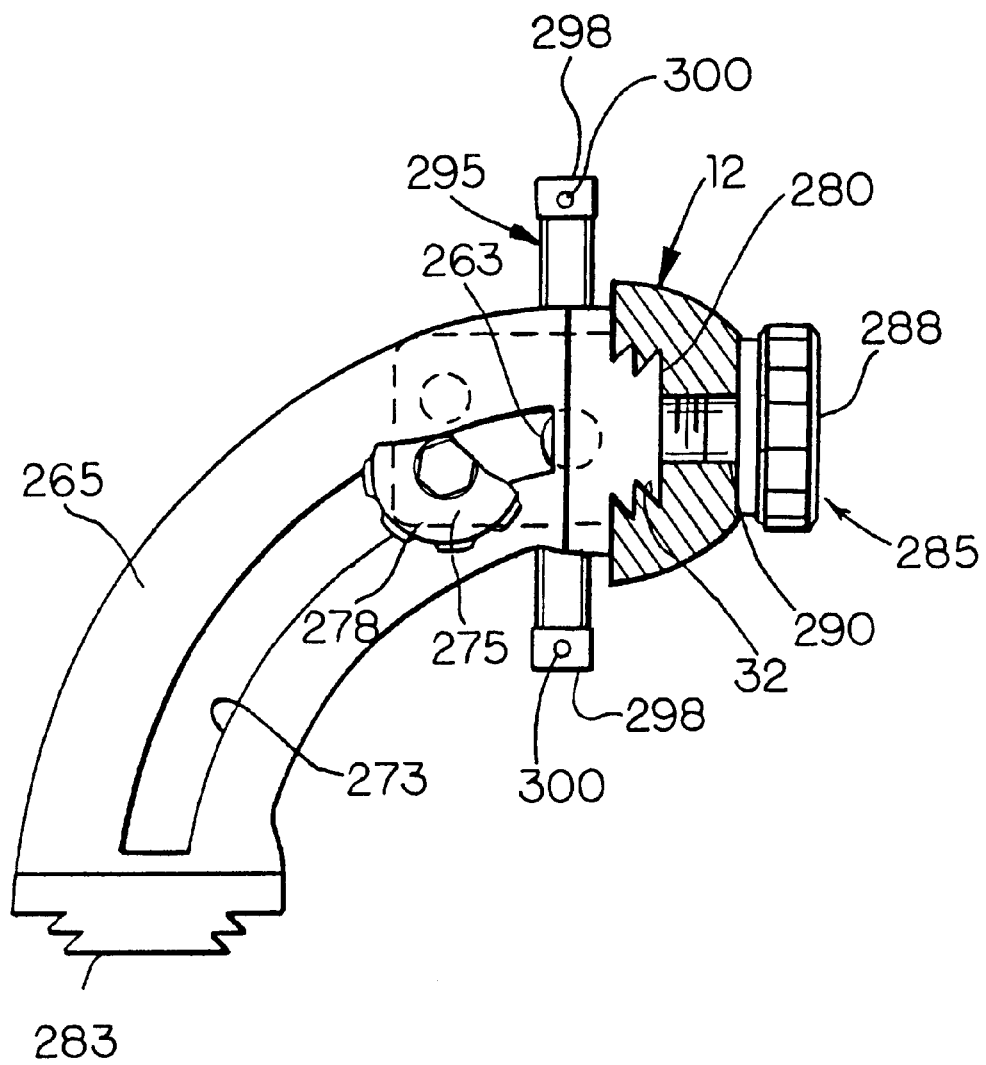
FIG. 12 is a bottom plan view of the distal clamp assembly of FIG. 10, to the scale of FIG. 10, showing the connection between the distal appendix and arcuate element.

Guide rail 12 defines a longitudinal rail axis R, and (as best seen in FIGS. 10 and 12) has a generally semicircular transverse cross-section and a flat rail face 30 with a central longitudinal rail groove 32 and an elongate rail slot 35. Rail groove 32 and slot 35 extend for nearly the entire length of guide rail 12 such that the rail groove and slot terminate short of the respective longitudinal ends of the guide rail.

Preferably, the longitudinal rail groove 32 has a double trapezoidal or dovetail shape, with the smaller side of the outer trapezoid being flush with rail face 30, as best seen in FIGS. 10 and 12. The rail groove 32 may alternatively have a single trapezoidal shape.

Proximal Clamp Assembly

Figure 2:
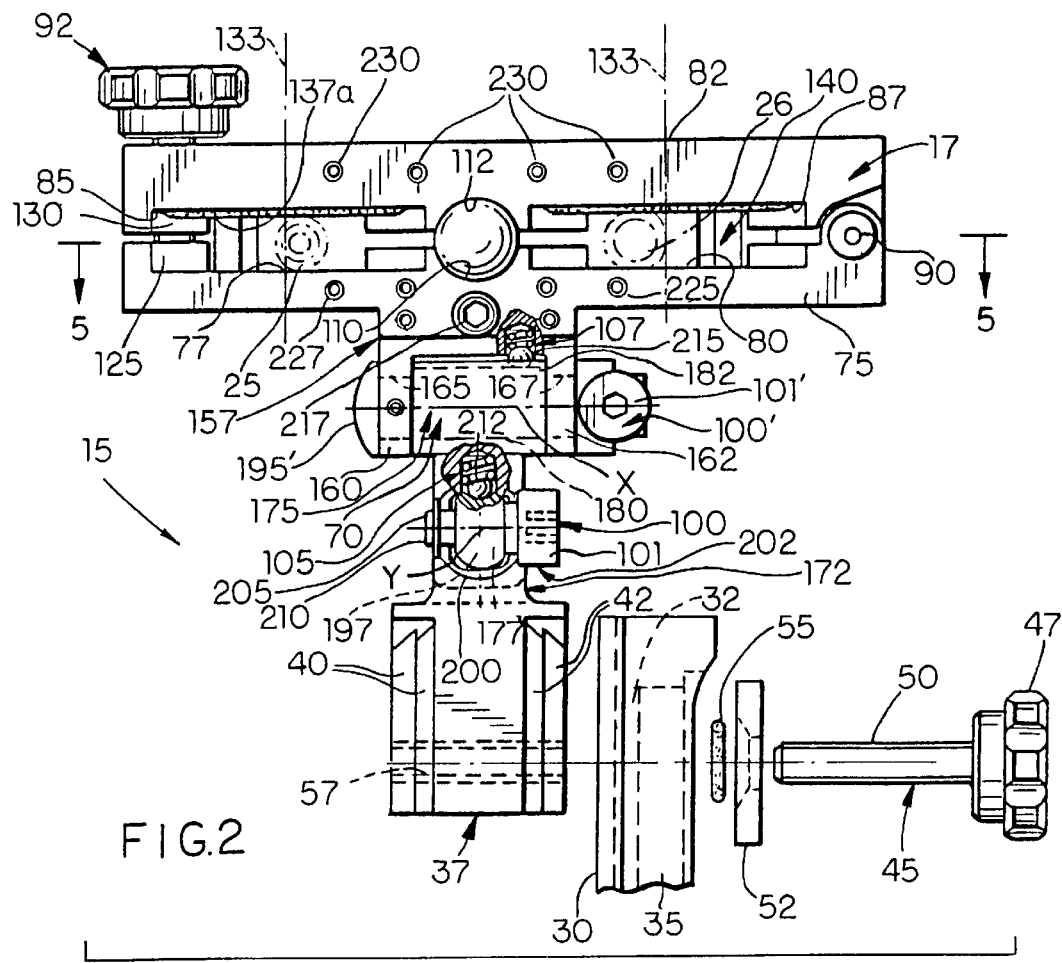
FIG. 2 is an enlarged-scale elevation view of the first or proximal clamp assembly of the fixator of FIG. 1 showing the cover in the closed position, with the alignment bracket being within the proximal bone screw clamp, part of the base foot and dual-axis joint being broken away to show the spring-loaded ball-detents, the assembly of one of the proximal tenons to the guide rail being shown in an exploded view.

As best seen in FIG. 2, the first or proximal clamp assembly 15 is substantially T-shaped, with a proximal anchor element 37 provided on its opposed faces with proximal tenons 40, 42 having a double dovetail cross section countershaped with respect to the longitudinal rail groove 32, for connection to guide rail 12. The proximal clamp assembly 15 is anchored to guide rail 12 by means of one of its proximal tenons 40, 42 inserted in rail groove 32, in proximity to one of its longitudinal ends where it is locked by means of a proximal rail screw 45.

More specifically, one of the proximal tenons, e.g., tenon 42 in FIG. 1, is locked to guide rail 12 by means of a proximal rail screw 45 having a knob 47, threaded shaft 50, and a metal washer 52 on shaft 50. Radial clearance exists between the hole in washer 52 and shaft 50 allowing the washer to freely translate longitudinally along the shaft 50. A resilient O-ring 55 is tightly held on shaft 50 opposite knob 47 to prevent the washer from separating from shaft 50.

Shaft 50 of proximal rail screw 45 extends through rail groove 32 and into a correspondingly threaded proximal tenon bore 57 with washer 52 disposed between knob 47 and guide rail 12. When knob 47 is rotated to screw shaft 50 into proximal tenon bore 57, the adjacent proximal tenon, e.g., tenon 42 in FIG. 1, is drawn into tight engagement with guide rail 12. As shown in FIG. 2, proximal tenon bore 57 extends through both proximal tenons 40, 42 allowing shaft 50 to be inserted into either tenon. The proximal anchor element 37 may thereby be anchored to the opposing faces of guide rail 12 shown in FIG. 2.

The upper ends of proximal tenons 40, 42 are outwardly flared to limit translation of the proximal tenons in rail groove 32 in the direction of rail axis R. The double dovetail cross section of the proximal tenons 40, 42 enables the proximal clamp assembly 15 to be used for both pediatric and adult applications since a single guide rail 12 may be used for both applications.

Alternatively, rail groove 32 and proximal tenons 40, 42 may have complementary cross sections having the shape of a single trapezoid. Such a shape for the cross section of proximal tenons 40, 42 and rail groove 32 may however, require guide rails 12 of different sizes for pediatric and adult applications.

Figure 4:
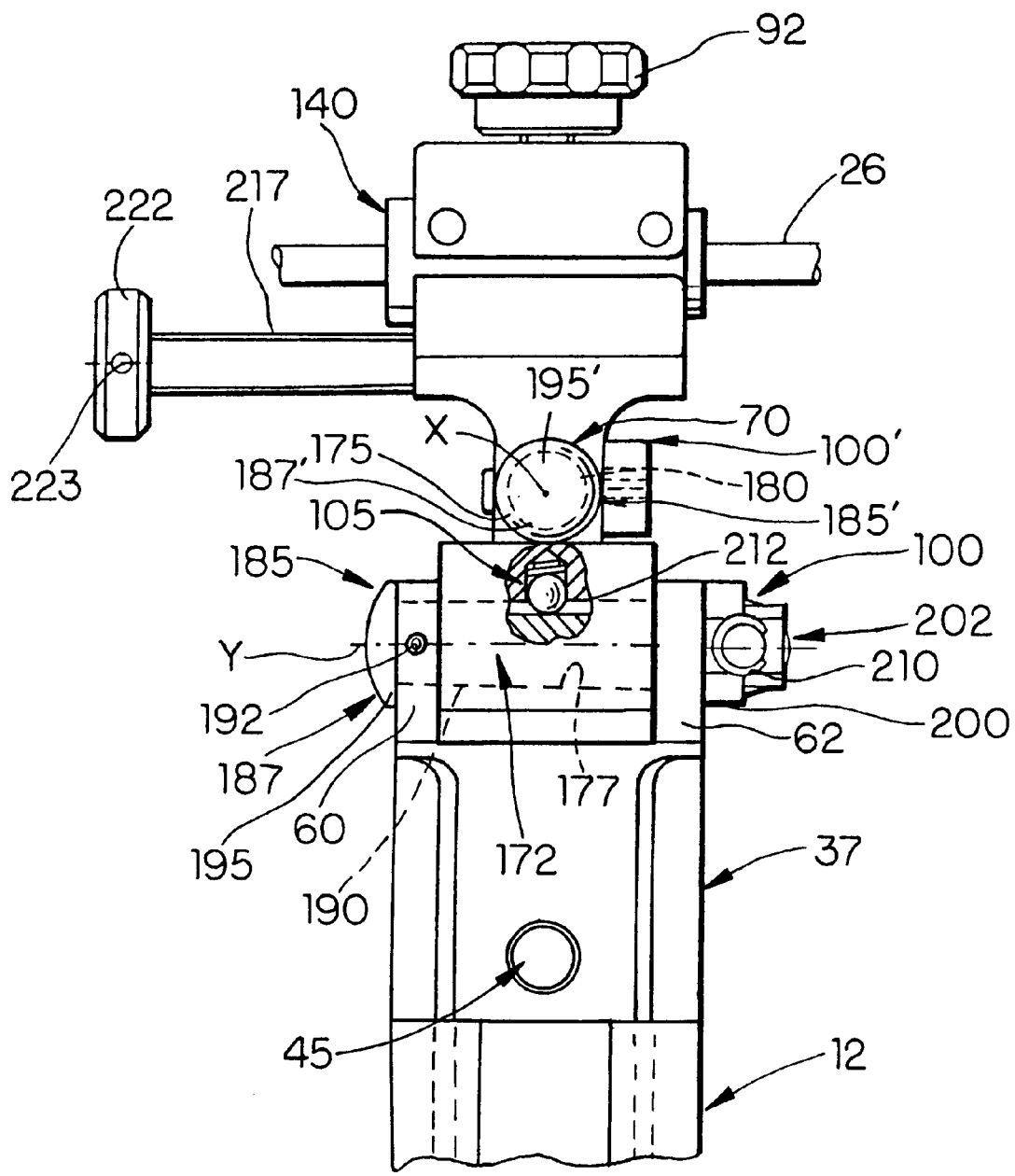
FIG. 4 is a side elevation of the clamp of FIG. 2, to the scale of FIG. 2, with part of the dual-axis hinge being broken away to show the spring-loaded ball-detent.

As shown in FIG. 4, proximal anchor element 37 includes a pair of upwardly extending integral anchor shoulders 60, 62 having a generally perpendicular orientation relative to proximal tenons 40, 42. Anchor shoulders 60, 62 have respective coaxial circular bores enabling a hinge connection to dual-axis joint 70, described hereinbelow.

A supporting portion or proximal bone screw clamp 17, for drill guides 25 for bone screws 26 insertable in the proximal portion of the bone B, is adjustably united to proximal base element 37 via dual-axis joint 70. Proximal clamp assembly 15 is in turn formed by a substantially flat base plate 75 with two base recesses 77, 80 upon which a cover 82, provided with complementary cover recesses 85, 87 is hinged at 90. Cover 82 is locked against base plate 75 by means of a jaw screw 92 so as to lock drill guides 25 for bone screws 26, with variable inclinations, between the recesses 77, 80, 85, 87.

Proximal bone screw clamp 17 is united to the proximal anchor element 37 by means of dual-axis joint 70 having a first or upper hinge axis X and a second or lower hinge axis Y, substantially perpendicular with respect to one another and with respect to the rail axis R when proximal clamp assembly 15 is anchored to guide rail 12. In order to selectively lock the angular position of dual-axis joint 70 with respect to proximal anchor element 37 about lower hinge axis Y, there is provided a lower eccentric stop or locking assembly 100 with a hexagonal set lower locking head 101. In order to selectively lock the angular position of dual-axis joint 70 with respect to the proximal bone screw clamp 17 about upper hinge axis X, there is provided an upper eccentric stop or locking assembly 100' also having a hexagonal set upper locking head 101'. In order to maintain the two axes X, Y in a preferential or "neutral" position, at one of several longitudinal grooves, spring-loaded ball-detent positioning means 105, 107 are provided, for detent engagement against a countershaped seat formed on each axis.

Figure 5:
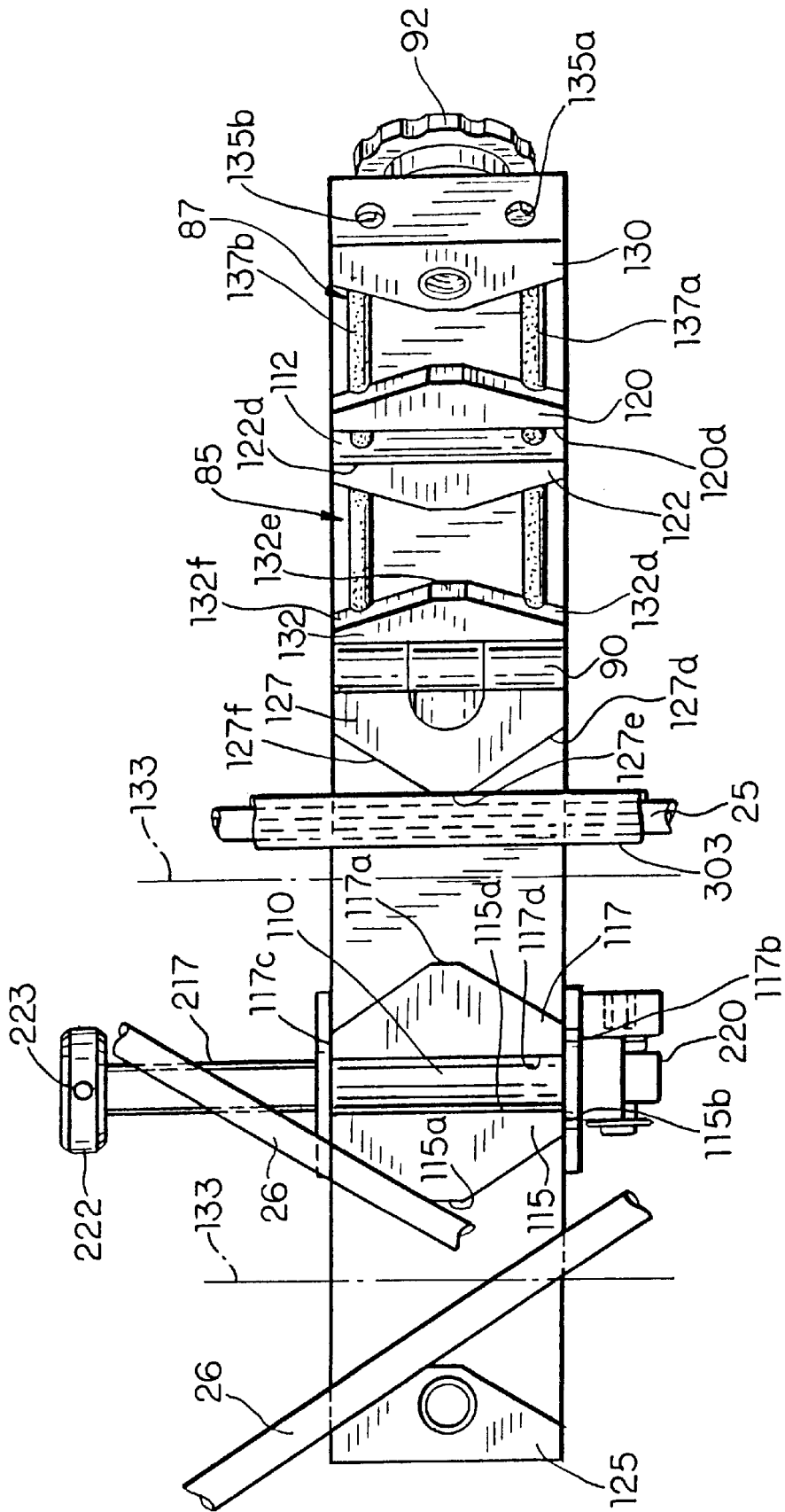
FIG. 5 is a view taken in the plane 5—5 of FIG. 2, to the scale of FIG. 2, showing the cover in the open position, and the inner contour of the base plate of the proximal bone screw clamp.

More specifically, hinge 90 enables cover 82 to swing, relative to base plate 75, between a closed position, shown in FIG. 2, and open positions one of which is illustrated in FIGS. 5 and 6. As shown in FIG. 2, the interior surfaces of base plate 75 and cover 82, in addition to having base and cover recesses 77, 80, 85, 87, are further contoured to include complementary transverse base and cover central recesses 110, 112 each having a semicircular cross section.

Also formed on the interior surfaces of base plate 75 and cover 82 are complementary generally triangular base and cover interior bosses 115, 117, 120, 122 and exterior bosses 125, 127, 130, 132, as shown in FIG. 5. The sides of generally triangular bosses 115, 117, 120, 122, 125, 127, 130, 132 are joined by flattened portions, such as flattened sides 117a, 117b, 117c of base interior boss 117. Base and cover interior bosses 115, 117, 120, 122 have sides 115d, 117d, 120d, 122d which are contiguous with longitudinal edges of semicircular recesses 110, 112. The height of the base and cover bosses 115, 117, 120, 122, 125, 127, 130, 132 is limited so that, when cover 82 is clamped to base plate 75, a space remains between each pair of opposing bosses, for example, 125, 130, as shown in FIG. 2. When cover 82 is in the closed position shown in FIG. 2, base and cover bosses 115, 117, 120, 122, 125, 127, 130, 132 are symmetrically disposed relative to a plane of symmetry 133.

Cover 82 has longitudinal front and rear cover grooves 135a, 135b each of which has closed ends with a circular cross section and an intermediate portion, with an arcuate cross section, between the ends. Cover grooves 135a, 135b open into cover recesses 85, 87. Rubber is injected into cover grooves 135a, 135b and, upon hardening, forms rods, longitudinal portions of which extend downward from the inner face of cover 82 resulting in formation of rubber cover ridges 137a, 137b, as shown in FIGS. 2 and 5. The rubber of cover ridges 137a, 137b is formed of a material which may be sterilized.

When cover 82 is clamped to base plate 75 with drill guides 25 or bone screws 26 therebetween, cover ridges 137a, 137b are compressed between the cover and drill guides, or between the cover and bone screws, for gripping thereof, thereby to resist translation of the drill guides and bone screws relative to proximal bone screw clamp 17. Such gripping will also be provided by cover ridges 137a, 137b with alignment bracket 140, described hereinbelow, seated on base plate 75.

The proximal clamp assembly 15 includes an alignment bracket 140 which may be clamped in proximal bone screw clamp 17 and removed therefrom, shown in FIGS. 2, 6 and 7. Alignment bracket 140 includes an elongate bracket base 142 with an upwardly extending central integral bracket tab 145 and upwardly extending integral bracket shoulders 147, 150 at opposite ends of the bracket base. Extending from one face of bracket tab 145 is a transverse cylindrical central bracket stem 152 with an integral bracket head 155 at the end opposite the bracket tab.

The bracket shoulders 147, 150 have complementary shapes, as viewed in FIG. 6, each being generally angular with two leg portions 147a, 150a and three alignment segments 147b, 147c, 147d, 150b, 150c, 150d subtended between the leg portions. The upper and lower surfaces of bracket shoulders 147, 150 are contained in the same respective upper and lower planes. The corner between leg portions 147a, 150a may alternatively be curved.

The contour of the upper interior surface of base plate 75 closely complements the lower surfaces of alignment bracket 140 so that, when the alignment bracket is seated on the base plate with bracket stem 152 received in base central recess 110 as shown in FIGS. 2 and 5, bracket base 142 adjoins a longitudinal edge of the base plate and bracket shoulders 147, 150 are lodged against respective base exterior bosses 125, 127. Alignment bracket 140 and the upper interior surface of base plate 75 are sized so that, when the alignment bracket is seated on the base plate as shown in FIG. 6, they closely fit together with little play therebetween. Bracket stem and head 152, 155 facilitate alignment of bracket base and shoulders 142, 147, 150 on the interior surface of base plate 75.

The complementary contours of the lower interior surface of cover 82 and the upper interior surface of base plate 75 is such that, when alignment bracket 140 is seated on the base plate and the cover is in the closed position as shown in FIG. 2, the cover and alignment bracket 140 similarly fit closely together with little play therebetween. Bracket stem and head 152, 155 facilitate retainment of bracket base and shoulders 142, 147, 150 between base plate 75 and cover 82 when the cover is in the closed position.

The symmetry between the contoured interior surfaces of base plate 75 and cover 82 enable alignment bracket 140 to be seated with bracket base 142 adjoining either the front or rear longitudinal edge of the base plate. When cover 82 is in the closed position shown in FIG. 2, bracket shoulders 147, 150 are symmetrically disposed relative to plane of symmetry 133. Placement of bracket base 142 against base plate 75 allows the portions of cover ridges 137a, 137b between bracket shoulders 147, 150 and cover interior bosses 120, 122 to remain exposed when cover 82 is in the closed position to provide the gripping described hereinabove.

The proximal bone screw clamp 17 includes an integral clamp foot 157 extending downwardly from the central portion of base plate 75. A pair of integral clamp shoulders 160, 162 extend downwardly from clamp foot 157 in generally transverse relation to base plate 75. Clamp shoulders 160, 162 have respective coaxial bores 165, 167 enabling a hinge connection to dual-axis joint 70, described hereinbelow. As shown in FIG. 2, clamp foot 157 has a socket, formed such as by drilling, adjacent to clamp shoulder 162, which opens to the lower surface of the footing for housing upper spring-loaded ball-detent positioning means 107, described hereinbelow.

The proximal bone screw clamp 17 is united to proximal anchor element 37 of the proximal clamp assembly 15 by means of dual-axis joint 70 having integral lower and upper joint portions 172, 175 each of which has a respective lower and upper hinge bore 177, 180 having respective central axes which define first and second hinge axes X, Y. The lower and upper joint portions 172, 175 are oriented relative to one another such that first and second hinge axes X, Y are offset orthogonal axes, i.e., axes X, Y do not intersect with one another, and each perpendicularly intersects a third axis such that first hinge axis X and the third axis define a plane which is orthogonal relative to a plane defined by second hinge axis Y and the third axis.

Lower joint portion 172 is disposed between anchor shoulders 60, 62 such that the bores therein are coaxial with hinge bore 177 and second hinge axis Y. Lower joint portion 172 is pivotally connected to proximal anchor element 37 by a lower hinge assembly 185 including a lower hinge bolt 187 having a shaft 190 extending through the bores in anchor shoulders 60, 62 and lower hinge bore 177. The portion of shaft 190 extending through lower joint portion 172 and anchor shoulders 60, 62 has a circular outer cross section which complements the circular cross sections of these bores. A radial clearance exists between shaft 190 and lower joint portion 172 allowing relative rotation therebetween. A transverse pin 192 extends through anchor shoulder 60 into shaft 190 to rotatably fix the shaft to the shoulder and, thereby, to proximal anchor element 37.

Lower hinge bolt 187 has an integral hinge bolt head 195 formed at one end of shaft 190. The end portion of shaft 190 outside of anchor shoulder 62, opposite bolt head 195, has a double D outer cross section and a transverse bore 197, as shown in FIG. 2. When shaft 190 is fully inserted through the coaxially aligned bores in anchor shoulders 60, 62 and lower joint portion 172, the inner surface of hinge bolt head 195 abuts the outer face of anchor shoulder 60 with transverse bore 197 extending beyond the outer face of anchor shoulder 62, as shown in FIG. 2.

Lower locking assembly 100 includes a lower hinge collar 200 which encircles hinge bolt shaft 190 between transverse bore 197 and anchor shoulder 62, as shown in FIGS. 2 and 4. Hinge collar 200 has a double D outer cross section and a generally rectangular inner cross section. The outer edges of the flattened portions of hinge collar 200 have a pair of diametrically opposed longitudinal recesses.

Lower locking assembly 100 further comprises a lower locking bolt 202 having a locking bolt shaft 205 with, at one end, integral hexagonal set lower locking head 101 and an integral annular eccentric portion between the lower locking head and shaft. Hexagonal set lower locking head 101 (e.g., "Allen" head) is rotatable by a complementary tool (e.g., "Allen" wrench).

When locking bolt shaft 205 is fully inserted through transverse bore 197 and across lower hinge collar 200, the annular eccentric portion of shaft 205, adjoining lower locking head 101, seats in one of the longitudinal recesses in lower hinge collar 200. The opposite end of shaft 205 seats in the other longitudinal recess in lower hinge collar 200.

Lower locking assembly 100 includes a lower spring clip 210 having an arcuate member and three integral radial tongues inwardly directed from the arcuate member such that the inner ends of the tongues extend into an annular groove in locking bolt shaft 205 and are resiliently held therein by the arcuate member. Lower spring clip 210 thereby obstructs removal of lower locking bolt shaft 205 from transverse bore 197, and consequently, obstructs removal of lower hinge bolt shaft 190 from lower hinge bore 177. Accordingly, lower joint portion 172 is pivotally connected to proximal anchor element 37.

Lower hinge assembly 185 allows rotation of lower joint portion 175 relative to proximal anchor element 37 when lower locking bolt shaft 205 is rotatably positioned with respect to lower hinge collar 200 so that the radially reduced portion of the annular eccentric portion of shaft 205 seats on the base of the longitudinal recess in collar 200.

The lower joint portion 175 and proximal anchor element 37 are locked in a desired angular alignment by rotating lower locking bolt shaft 205 counterclockwise, using the complementary tool for lower locking head 101. The direction of such rotation is indicated by an arrow pointing in the direction of counterclockwise rotation inscribed on the outer face of lower locking head 101.

Counterclockwise rotation of lower locking bolt shaft 205 causes the radially enlarged section of the annular eccentric portion of shaft 205 to ride up on the base of the longitudinal recess in collar 200. Such "riding up" of eccentric portion causes the transverse bore 197 in the end of lower hinge bolt shaft 190 to translate away from anchor shoulder 62 producing tension in lower hinge bolt shaft 190 thereby compressing anchor shoulders 60, 62 against lower joint portion 172. Anchor shoulders 60, 62 are thereby frictionally locked against lower joint portion 172 in a desired relative angular alignment.

Anchor shoulders 60, 62 and lower joint portion 172 may be unlocked by rotating lower locking head 101 in the opposite direction allowing the radially enlarged section of the annular eccentric portion of shaft 205 to ride down from the base of the longitudinal recess in lower hinge collar 200 thereby relieving the tension in lower hinge bolt shaft 190. Also inscribed on the outer face of lower locking head 101 is a dimple to indicate if lower locking bolt 202 is in the locked position, e.g., positioning the dimple at 5 o'clock may indicate the locking bolt is locked while positioning the dimple at "3 o'clock" may indicate the locking bolt is unlocked.

Lower positioning means 105 includes a spring-loaded ball-detent 212 supported in a socket formed, as by drilling, in the upper section of lower joint portion 172 and biased radially downwardly by the spring, as shown in FIGS. 2 and 4. When lower joint portion 172 is rotatably positioned relative to proximal anchor element 37 such that the socket in lower joint portion 172 aligns with the a longitudinal detent groove on the upper surface of shaft 190, ball-detent 212 is urged by the spring into seating engagement with the detent groove thereby resisting rotation of the lower joint portion away from this angular position relative to proximal anchor element 37, which defines the neutral position. The neutral position of lower joint portion 172, relative to proximal anchor element 37, is generally upright as viewed in FIGS. 3 and 4.

A moderate rotation force, however, applied to lower joint portion 172, when in the neutral position, will cause rotation thereof relative to proximal anchor element 37 resulting in lower ball-detent 212 riding up out of the detent groove on shaft 190 onto the outer surface thereof. The radial spring force applied to lower ball-detent 212 will thereby be overcome and the ball-detent will roll along the outer surface of shaft 190. The resistance to rotation of lower joint portion 172 by ball-detent 212 will be correspondingly reduced.

Upper joint portion 175 is disposed between clamp shoulders 160, 162 such that the bores in the clamp shoulders are coaxial with upper hinge bore 180 and first hinge axis X. Upper joint portion 175 is pivotally connected to proximal bone screw clamp 17 by an upper hinge assembly 185'. Each part of upper hinge assembly 185' has a counterpart in lower hinge assembly 185. Accordingly, the parts of upper hinge assembly 185' are identified by the same reference numerals used for lower hinge assembly 185 with the addition of a "'".

It should be noted, however, that upper hinge bolt shaft 190' does not have a longitudinal groove on the outer surface thereof, in contrast to that of the lower hinge bolt shaft 190 which receives the ball-detent of positioning means 105. Otherwise, the parts are similar. Proximal bone screw clamp 17 may therefore pivot relative to dual-axis joint 70 by means of upper hinge assembly 185', in the manner described above in connection with lower hinge assembly 185.

Coupled to the end of upper hinge bolt shaft 190' opposite upper hinge bolt head 195' is upper locking assembly 100'. Each part of upper locking assembly 100' has a counterpart in lower locking assembly 100. Accordingly, the parts of upper locking assembly 100' are identified by the same reference numerals used for lower locking assembly 100 with the addition of a "'". Proximal bone screw clamp 17 may therefore be locked in various predetermined angular orientations relative to dual-axis joint 70 by means of upper locking assembly 100', in the manner described above in connection with lower locking assembly 100.

Upper positioning means 107 includes a spring-loaded ball-detent supported in the socket in clamp foot 157 and biased downwardly by the spring, as shown in FIG. 2. A portion of upper ball-detent 215, upon urging by the spring-loading, extends beyond the lower surface of clamp foot 157. When proximal bone screw clamp 17 is rotatably positioned relative to upper joint portion 175 such that the hole in clamp foot 157 aligns with a longitudinal detent groove 182 formed in the upper surface of the upper joint portion, upper ball-detent 215 is urged by the spring-loading of upper positioning means 107 into seating engagement with the detent groove thereby resisting rotation of proximal bone screw clamp 17 away from this angular position relative to upper joint portion 175, which defines the neutral position. The neutral position of the proximal bone screw clamp 17, relative to upper joint portion 175, is generally upright as viewed in FIGS. 2 and 4.

A moderate rotation force, however, applied to proximal bone screw clamp 17, when in the neutral position, will cause rotation thereof relative to upper joint portion 175 resulting in upper ball-detent 215 riding up out of detent groove 182 onto the outer surface of the upper joint portion. The spring force applied to upper ball-detent 215 will thereby be overcome and the ball-detent will roll along the outer surface of upper joint portion 175. The resistance to rotation of proximal bone screw clamp 17 by upper ball-detent 215 will be correspondingly reduced.

Figure 3:
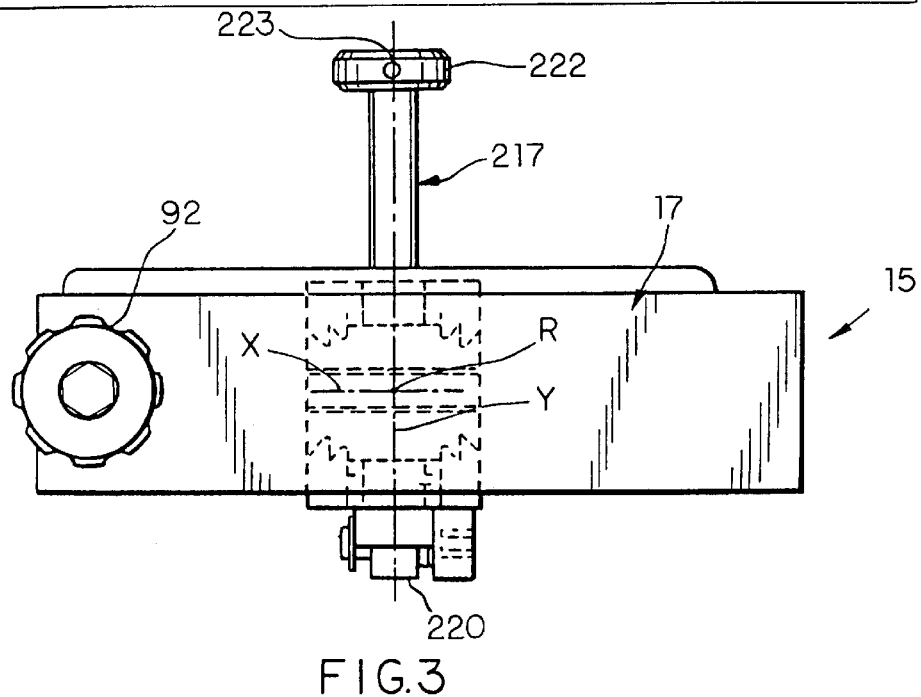
FIG. 3 is a top plan view of the proximal clamp assembly of FIG. 2, to the scale of FIG. 2, showing the tenon connection between the proximal clamp assembly and guide rail in hidden lines.

As shown in FIG. 3, there are provided proximal distancing means constituted by a proximal distancing screw 217 which is screwed in a threaded hole formed in the central part of base plate 75 and having a hexagonal set proximal distancing head 220 (e.g., "Allen" head) rotatable by a complementary tool (e.g., "Allen" wrench). Proximal distancing screw 217 also has a proximal abutment end 222 supportable at bone B. Proximal abutment end 222 is fixed to the shaft of proximal distancing screw 217 by a transverse pin 223. Proximal abutment end 222 is displaced relative to base plate 75 by rotating proximal distancing screw 217.

Other proximal distancing means, for rigidly holding a portion of bone B in position during drilling, are constituted by Kirschner wires 225 fixed in bone B and passing through calibrated holes 227 provided in base plate 75 and calibrated holes 230 provided in cover 82. When alignment bracket 140 is clamped in proximal bone screw clamp 17, calibrated holes 227 in base plate 75 may be partially obstructed by bracket base 142.

Figure 8:
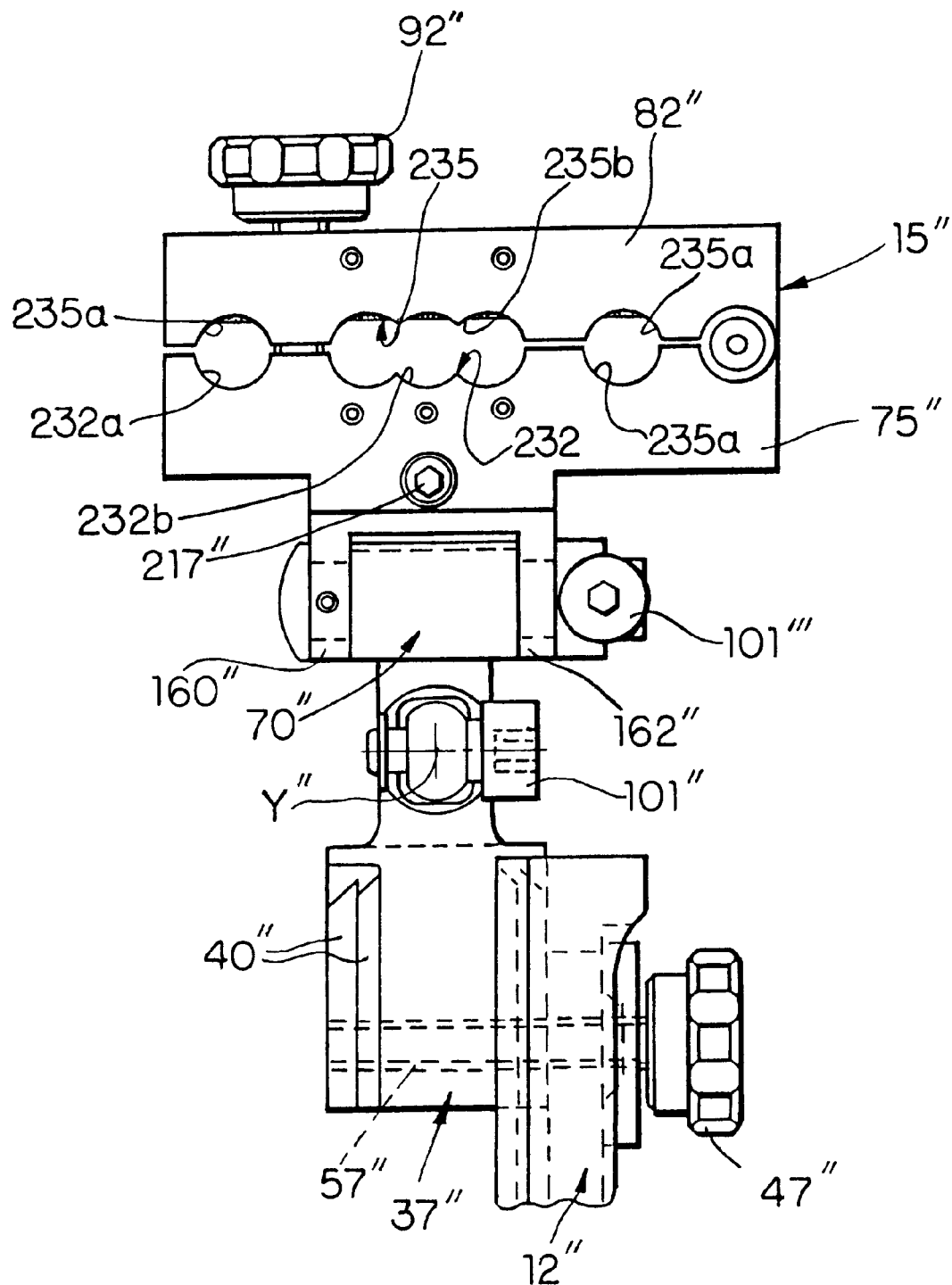
FIG. 8 is a view in the direction of FIG. 2, to the scale of FIG. 2, showing a second embodiment of the proximal bone screw clamp with one of the proximal tenons shown assembled to the guide rail, the cover being in the closed position.
Figure 9:
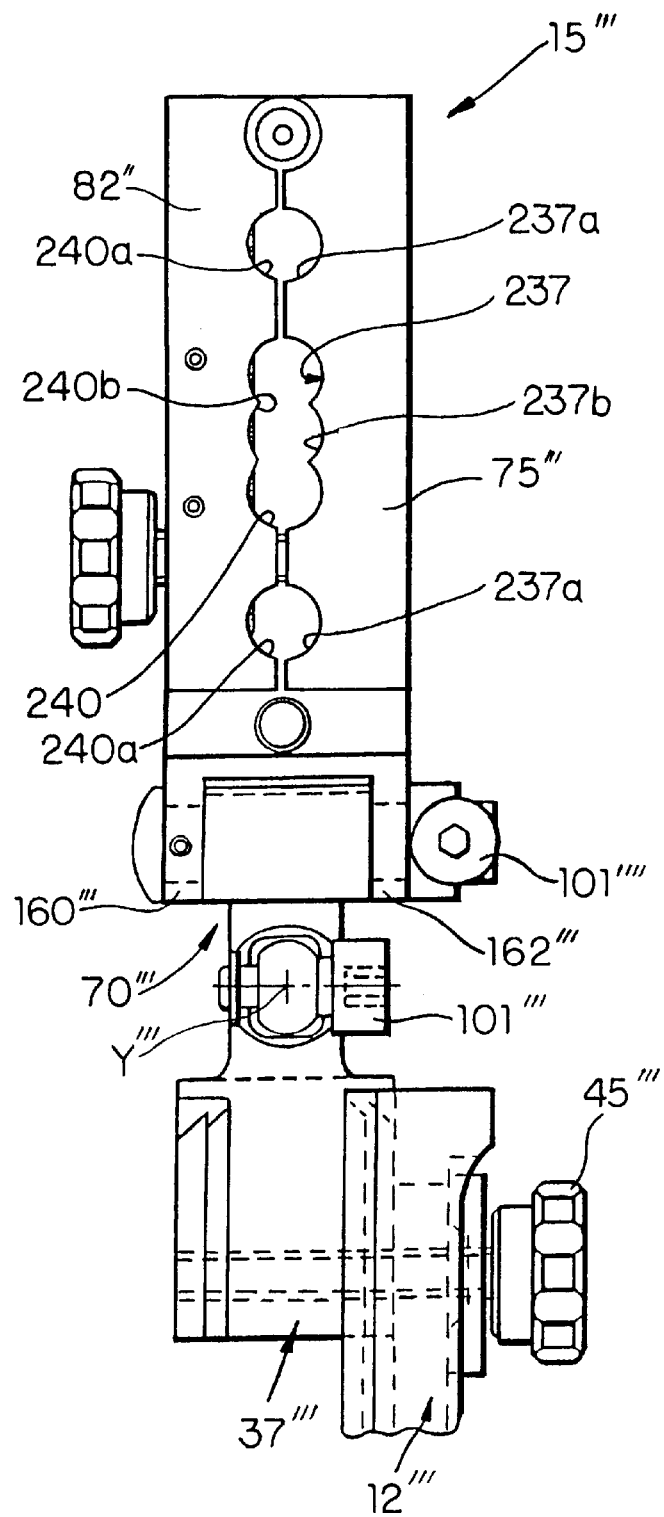
FIG. 9 is a view in the direction of FIG. 2, to the scale of FIG. 2, showing a third embodiment of the proximal bone screw clamp with one of the proximal tenons being shown assembled to the guide rail.

FIGS. 8 and 9 illustrate second and third alternative embodiments of proximal bone screw clamp 15. Each part of proximal bone screw clamps 15', 15" have a counterpart in proximal bone screw clamps 15 shown, for example, in FIG. 2. Accordingly, the reference characters of FIG. 2 are used to represent corresponding parts in FIGS. 8 and 9 with the addition of "''", "'''" in the figures of the second and third embodiments, respectively. Proximal bone screw clamps 15", 15''' differ from proximal bone screw clamp 15 in that the inner faces of base plates 75", 75''' and covers 82", 82''' have facing proximal seats 232, 235, 237, 240 for supporting drill guides 25 for bone screws 26. Proximal seats 232, 235 of proximal bone screw clamp 15" include two elongate arcuate outer recesses 232a, 235a and three elongate arcuate inner recesses 232b, 235b all of which are parallel to one another, as shown in FIG. 8. Inner recesses 232b, 235b adjoin one another to define a scalloped cross section. Outer recesses 232a, 232a are transversely symmetrical relative to inner recesses 232b, 235b.

Proximal seats 237, 239 of proximal bone screw clamp 15''' include two elongate arcuate outer recesses 237a, 239a and three elongate arcuate inner recesses 237b, 239b all of which are parallel to one another, as shown in FIG. 9. Inner recesses 237b, 239b adjoin one another to define a scalloped cross section. Outer recesses 237a, 239a are transversely symmetrical relative to inner recesses 237b, 239b.

Proximal bone screw clamp 15''' differs from proximal bone screw clamp 15 in that the inner faces of base plate 75''' and cover 82''' are parallel to clamp shoulders 160''', 162'''. As a result, proximal clamp assembly 15''' has a generally elongate shape, when proximal bone screw clamp 15''' and dual-axis joint 70''' are in the neutral positions, as compared to the generally T-shapes of the proximal clamp assemblies 15, 15", as viewed in FIGS. 2 and Inscribed on the sides of base plates 75", 751''' is the phrase "PEDIATRIC USE" and a series of three laterally disposed, equally spaced semi-circles having co-linear centers and connected ends. This is to indicate that, when proximal bone screw clamps 17", 17''' are used to support drill guides 25 for inserting bone screws 26 into bone B in a pediatric application, the drill guides may be seated in outer recesses 232a, 235a, 237a, 240a and the middle recess of inner recesses 232b, 235b, 237b, 240b, sometimes referred to as the "1–3–5" positions. Proximal bone screw clamps 17", 17''' may also support bone screws 26 in these positions for pediatric applications.

In contrast, in adult applications, two or three drill guides 25 may be supported in proximal bone screw clamps 71", 17''', in positions such as the "1–3–5", which may be most stable, or the "1–2–4". Bone screws 26 may also be seated in these positions in adult applications.

Distal Clamp Assembly

The second or distal clamp assembly 20 is essentially constituted by a second supporting portion or distal bone screw clamp 22, in turn formed by a distal base 243 upon which a distal cover 245 is hinged at 248. Distal base 243 and cover 245 have facing distal seats 250, 253 for holding drill guides 25 for bone screws 26 insertable in the distal portion of the bone B by means of a locking action provided by a distal clamp screw 255 with a knob 258.

Figure 11:
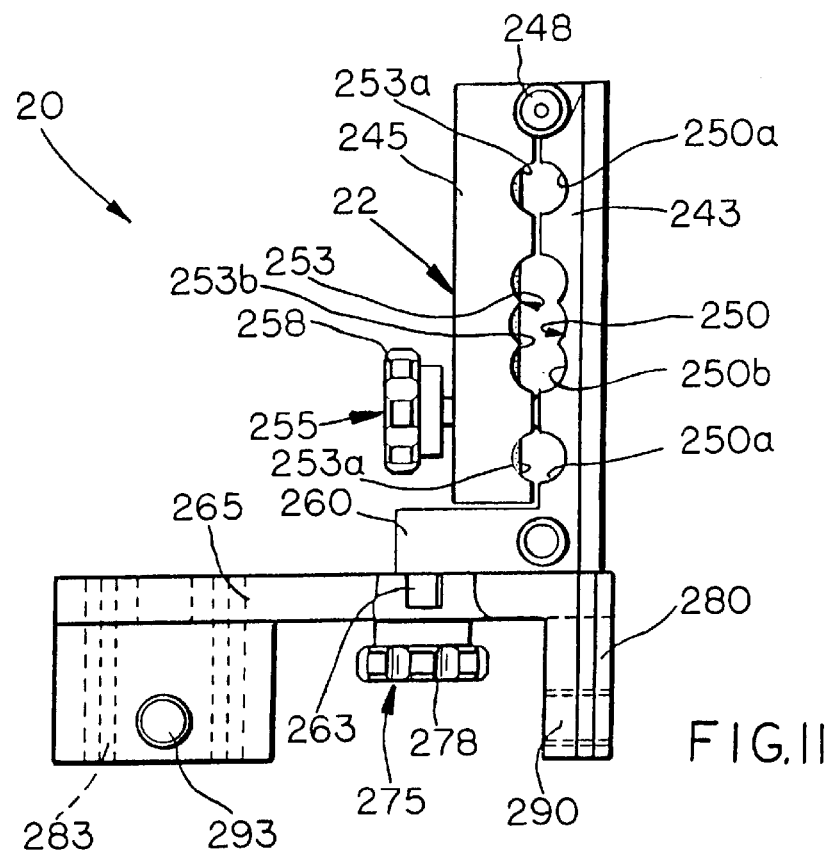
FIG. 11 is an elevation view of the distal clamp assembly of FIG. 10, to the scale of FIG. 10.

Distal seats 250, 253 include two elongate arcuate outer recesses 250a, 253a and three elongate arcuate inner recesses 250b, 253b all of which are parallel to one another, as shown in FIG. 11. Inner recesses 250b, 253b adjoin one another to define a scalloped cross section. Outer recesses 250a, 253a are transversely symmetrical relative to inner recesses 250b, 253b.

Inscribed on the side of distal base 243 is the phrase "PEDIATRIC USE" and a series of three laterally disposed, equally spaced semi-circles having co-linear centers and connected ends. This inscription has a similar meaning as that on base plates 75', 75", described hereinabove.

Protruding from distal base 243 is an integral distal appendix 260 opposite from hinge 248. Distal appendix 260 has a distal end pin 263 extending from the face opposite distal cover 245. Distal appendix 260 also has a pair of threaded appendix bores, each of which has a central axis parallel to end pin 263.

The distal clamp assembly 20 further includes a transversal circular arc element 265 having a center 268, and on one of its flat faces a graduated scale 270 for measuring the torsion angle of distal bone screw clamp 22. Arc element 265 also has an arcuate groove 273, as shown in FIGS. 10 and 12.

Distal appendix 260 is assembled to arc element 265 by inserting distal end pin 263 into arcuate groove 273 and aligning one of the appendix bores of distal appendix 260 with arcuate groove 273. The threaded shaft of appendix screw 275 is inserted into one of the threaded appendix bores in distal appendix 260 such that arc element 265 is sandwiched between the knob 278 of appendix screw 275 and the distal appendix.

Appendix screw 275 is threadedly engaged with the one appendix bore of distal appendix 260 by rotating knob 278. Alternatively, knob 278 may be replaced by a hexagonal head (e.g., "Allen" head) rotatable by a complementary tool (e.g., "Allen" wrench).

Distal bone screw clamp 22 is thereby coupled to arc element 265 and translatable relative thereto along arcuate groove 273 by limiting the tightening of appendix screw 275 in the one appendix bore of distal appendix 260 so that a clearance remains between the distal appendix and arc element 265. To lock the angular position of distal bone screw clamp 22 relative to arc element 265, appendix screw 275 is tightened to tightly clamp distal appendix 260 against the arc element.

Distal rail screw 285 may include a metal washer between knob 278 and arc element 265. Radial clearance may exist between the hole in such a washer and the shaft of screw 285 allowing the washer to freely translate longitudinally along the shaft of the distal radial screw. In such an assembly, a resilient O-ring may be tightly held on the shaft opposite knob 278 to prevent the washer from separating from the shaft.

At the extremities of the flat arc element 265, there are formed connection or distal tenons 280, 283 depending from the arc element, as viewed in FIG. 11. Distal tenons 280, 283 having a double dovetail cross section countershaped with respect to the longitudinal rail groove 32. Distal tenons 280, 283 permit a right or left mounting on guide rail 12 according to the requirements. The double dovetail cross section of the distal tenons 280, 283 enables distal clamp assembly 20 to be used for both pediatric and adult applications. Alternatively, rail groove 32 and distal tenons 280, 283 may have complementary cross sections having the shape of a single trapezoid, with similar results on pediatric and adult applications as described hereinabove for proximal tenons 40, 42.

Distal tenons 280, 283 may be inserted in rail groove 32 of guide rail 12 and be locked in position by means of a distal rail screw 285 with a knob 288 which is screwed in respective threaded distal tenon holes or bores 290, 293 formed in correspondence with distal tenons 280, 283. Knob 288 may be of the hexagonal type (e.g., "Allen" head) rotatable by a complementary tool (e.g., "Allen" wrench).

The center 268 of arcuate groove 273 should coincide approximately with the axis of bone B when distal clamp assembly 20 is mounted on guide rail 12 and defines a third correction axis Z, perpendicular to the first and second hinge axes X, Y of the distal portion of the bone B affected by torsion.

The distal clamp assembly 20 includes a distal distancing means constituted by a distal distancing screw 295 which is screwed in a threaded bore formed in the side of distal appendix 260 and having distal abutment ends 298 adapted to be supported at the distal portion of bone B to be corrected in a similar manner as by the proximal distancing means, described hereinabove. Distal abutment ends 298 are each fixed to the shaft of distal distancing screw 295 by a transverse pin 300. Distal abutment ends 298 are displaced relative to distal appendix 260 by rotating distal distancing screw 295.

Operation

In operation, the surgeon obtains with x-rays on multiple planes the angles of the angular defects of the proximal portion and of the torsion defects of the distal portion of bone B, and then imposes and locks such angles on the proximal and distal clamp assemblies 15, 20 and mounts the latter on the guide rail 12. Thereafter the drilling of the bone B in correspondence with the proximal and distal portions of the bone B is carried out by using the drilling guides locked on the proximal and distal clamp assemblies 15, 20. Then the osteotomy of the bone B in correspondence with the proximal and distal portions thereof is carried out and the proximal and distal clamp assemblies 15, 20 are brought back in correct position towards the rest position imposed by the preferential positioning means, such as positioning means 105, 107, eliminating the angular defects of the bone. Finally, the proximal and distal clamp assemblies 15, 20 of the apparatus 10 are substituted with those of an external fixator which sustains the limb for the entire period of growth of the bone callous up to complete recovery.

More specifically, proximal and distal bone screw clamps 17, 22 may clamp to drill guides 25, bone screws 26 and screw guides 303, depending on the application. A screw guide 303 is tubular having a typical outer diameter of 8 mm. The inner diameter of screw guide 303 is slightly larger than the outer diameter of a drill guide 25 or bone screw 26, typically 6 mm, allowing insertion of either into the screw guide. A drill guide 25 is tubular having an inner diameter which is slightly larger than a drill bit, which is sized to drill holes, typically 4.8 mm diameter, into bone B into which bone screws 26, typically 6 mm diameter, threadedly engage.

An advantage of screw guides 303 is that, if the orthopaedic apparatus 10 is used to position drill guides 25 for boring holes in bone B, the drill guides may be removed from the screw guides after such boring and replaced with bone screws without having to open bone screw clamps 17, 22 or otherwise disturb clamp assemblies 15, 17. Orthopaedic apparatus 10 may then be used to manipulate bone B.

Drill guides 25, bone screws 26 and screw guides 303 may have a variety of orientations relative to proximal bone screw clamp 17 as a result of the contouring of the interior opposing faces of base plate 75 and cover 82, illustrated in FIG. 5. Each opposing pair of bosses, for example base and cover exterior bosses 127, 132 each provide three sets of complementary faces 127d, 127e, 127f, 132d, 132e, 132f for orienting drill guides 25, bone screws 26 and screw guides 303 in three different orientations relative to base plate 75 and cover 82.

Alignment bracket 140 provides additional orientations for drill guides 25, bone screws 26 and screw guides 303, as illustrated in FIG. 6. Each bracket shoulder, for example shoulder 150, provide three sets of faces, 150b (in conjunction with face 127d of base exterior boss 127), 150c, 150d for orienting drill guides 25, bone screws 26 and screw guides 303 in three different orientations relative to base plate 75 and cover 82.

Orthopaedic apparatus 10, with drill guides clamped in proximal or distal bone screw clamps 17, 22, may be advantageously used to drill holes in the proximal and distal portions of bone B at preselected angles for insertion of bone screws 26 therein at such angles. Such preselected angles may be achieved by orienting drill guides 25 relative to proximal bone screw clamp 17, as described hereinabove, or by manipulating proximal or distal bone screw clamps 17, 22 about axes X, Y, Z, R, as described hereinbelow.

The orientations of proximal and distal clamp assemblies 15, 20 are adjustable about the four axes X, Y, Z, R, as follows. Proximal bone screw clamp 17 may be pivoted relative to proximal anchor element 37 about the first and second hinge axes X, Y by virtue of dual-axis joint 70. Such pivoting applies a bending moment to bone B thereby to tend to change the curvature of the bone between the connections thereof to proximal and distal clamp assemblies 15, 20.

Distal bone screw clamp 22 may be arcuately translated relative to distal tenons 280, 283 about correction axis Z because of the coupling between distal appendix 260 and arc element 265. Such relative translation imparts torsion to bone B about axis Z thereby to tend to twist the bone between the connections thereof to proximal and distal clamp assemblies 15, 20.

Distal tenons 280, 283 may translate relative to guide rail 12 parallel to rail axis R by virtue of the coupling therebetween. Such relative translation imparts axial tension or compression to bone B about axis Z thereby to tend to change the length of the bone between the connections thereof to proximal and distal clamp assemblies 15, 20. When making adjustments about any of axes X, Y, Z, R, it may be desirable to fix the orientation of the respective clamp assemblies 15, 20 about the other three axes.

Figure 13:
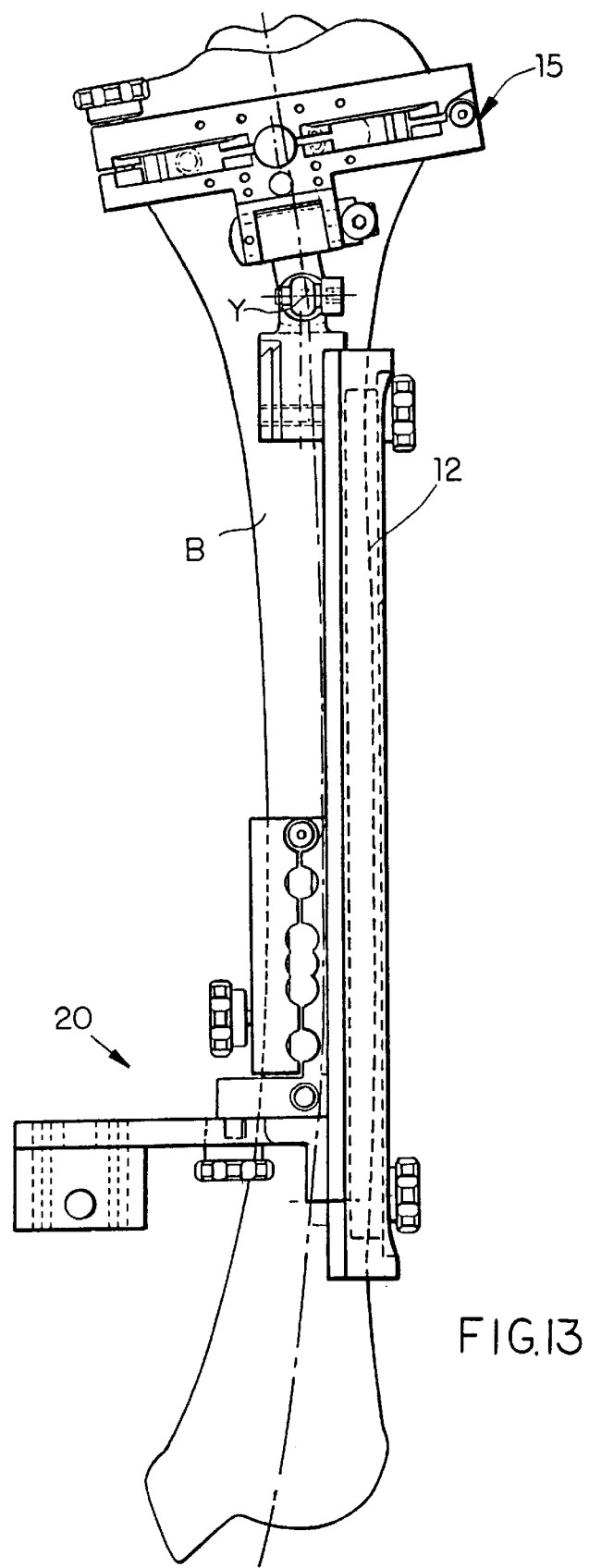
FIG. 13 is a front-elevation view of the fixator of FIG. 1, to the scale of FIG. 1, applied to a bone before correction.

Orthopaedic apparatus 10, when proximal and distal bone screw clamps 17, 22 are clamped to screw guides 303 containing bone screws 26 or directly to the bone screws of a deformed bone B may be used to reposition the bone about any of axes X, Y, Z and R by manipulating proximal and distal clamp assemblies 15, 20. For example, the misshaped bone B illustrated in FIG. 13, to which proximal and distal clamp assemblies 15, 20 are clamped in accordance with the teachings of the present invention, is corrected to the shape shown in FIG. 1 by pivoting proximal bone screw clamp 17 relative to guide rail 12 about axis Y. Before manipulation of bone B, sections thereof transverse to the central axis thereof may be removed to facilitate the manipulation.

What is claimed is:

1. Orthopaedic apparatus comprising a longitudinal rod externally positionable substantially parallel to a bone for correction, a first clamp movably anchored to said rod for supporting drilling guides for screws insertable in a proximal portion of the bone, and at least one second clamp movably anchored to said rod for supporting drilling guides for screws insertable in a distal portion of the bone, said first and second clamps being orientable and selectively lockable, before the surgical intervention, in predetermined angular positions with respect to said longitudinal rod corresponding to the angular deformations of the bone, and being repositionable with respect to said rod thereby to manipulate the bone to a correct shape and to retain the bone in the correct shape, said first clamp having a supporting portion for said drilling guides and a preferential positioning means for maintaining said supporting portion in an operative position with respect to said rod, said preferential positioning means having an elastically compressible detent means for allowing pivoting displacement of said first clamp away from said operative position when sufficient pivoting force is applied to said supporting portion.

2. Orthopaedic apparatus according to claim 1, wherein said supporting portion is united to a first portion for connection to said rod by means of first and second mutually perpendicular hinging axes.

3. Orthopaedic apparatus according to claim 1, wherein a connection portion of said first clamp is anchorable to said rod such that said first and second hinging axes are perpendicular to the longitudinal axis of the rod.

4. Orthopaedic apparatus according to claim 1, wherein said preferential positioning means is adapted for maintaining said supporting portion substantially orthogonal with respect to said rod when said supporting portion is in said operative position.

5. Orthopaedic apparatus according to claim 4, wherein said detent means is of the sphere type elastically compressed in a centering seat of said first clamp, said centering seat being formed on a hinging axis about which said supporting portion is adapted to pivot relative to said rod.

6. Orthopaedic apparatus according to claim 1, wherein said supporting portion comprises a base plate, a cover hinged on said base and a locking knob for locking said cover against said base locking therebetween the drilling guides.

7. Orthopaedic apparatus according to claim 1, wherein said first clamp has adjustable distancing means for positioning said supporting portion with respect to the facing bone portion.

8. Orthopaedic apparatus according to claim 7, wherein said distancing means comprise a screw screwed in a threaded hole provided in a substantially central position of said base plate.

9. Orthopaedic apparatus according to claim 7, wherein said distancing means comprise one or more Kirschner wires insertable in the proximal portion of the bone in calibrated holes formed in said base plate and in said cover.

10. Orthopaedic apparatus comprising a longitudinal rod externally positionable substantially parallel to a bone for correction, a first clamp movably anchored to said rod for supporting drilling guides for screws insertable in a proximal portion of the bone, and at least one second clamp movably anchored to said rod for supporting drilling guides for screws insertable in a distal portion of the bone, said first and second clamps being orientable and selectively lockable, before the surgical intervention, in predetermined angular positions with respect to said longitudinal rod corresponding to the angular deformations of the bone, and being repositionable with respect to said rod thereby to manipulate the bone to a correct shape and to retain the bone in the correct shape,
wherein said second clamp comprises a second supporting portion for the drilling guides connected to a second portion for connecting to said rod by means of circular arcuate guide means with an axis substantially coincident with the axis of the bone to be corrected.

11. Orthopaedic apparatus according to claim 10, wherein said circular arcuate guide means extend in a transversal plane when said second connecting portion is anchored to said rod.

12. Orthopaedic apparatus according to claim 1, wherein said second clamp comprises a base and a cover as well as screw distancing means for maintaining said second clamp at a predetermined distance with respect to the distal portion of the bone to be corrected.

13. Orthopaedic apparatus comprising a longitudinal rod externally positionable substantially parallel to a bone for correction, a first clamp movably anchored to said rod for supporting drilling guides for screws insertable in a proximal portion of the bone, and at least one second clamp movably anchored to said rod for supporting drilling guides for screws insertable in a distal portion of the bone, said first and second clamps being orientable and selectively lockable, before the surgical intervention, in predetermined angular positions with respect to said longitudinal rod corresponding to the angular deformations of the bone, and being repositionable with respect to said rod thereby to manipulate the bone to a correct shape and to retain the bone in the correct shape,
wherein said second clamp comprises a base and a cover as well as screw distancing means for maintaining said second clamp at a predetermined distance with respect to the distal portion of the bone to be corrected,
wherein said rod has a longitudinal seat with a substantially trapezoidal transverse cross section for slidably holding first and second connecting portions with respective dovetail shapes of said clamps.

14. A fixator for use in correcting a bone deformity comprising:
an elongate guide rail having a longitudinal axis and at least one elongate generally flattened face;
first and second clamp assemblies each having respective first and second anchor elements at least one of which is adjustably positionable in one of said respective proximal and distal regions of said guide rail on said face thereof, said first and second anchor elements being keyed to said guide rail face to fix said first and second clamps thereto and to limit said adjustable positioning to translation in the direction of said guide rail axis,
said first and second clamp assemblies having respective first and second bone screw clamps,
said first clamp assembly having a dual-axis joint for connecting said first bone screw clamp to said associated anchor element, said dual-axis joint defining offset orthogonal axes one of which is fixed relative to said rail axis,
said first clamp assembly further having means for locking said first bone screw clamp at selected angles about said orthogonal axes relative to said rail axis,
said second anchor element including an appendix having a surface in a plane transverse to said rail axis, said appendix having means for providing arcuate translation of said second bone screw clamp in said transverse plane relative to said rail axis,
said second clamp assembly further including means for locking said second bone screw clamp to said appendix at selected positions along said arcuate path relative to said rail axis.

15. A fixator as set forth in claim 14 wherein said anchor elements are keyed to said guide rail by a dovetail joint.

16. A fixator as set forth in claim 14 wherein said one bone screw clamp of said first clamp assembly includes a flat interior seat surface for supporting a plurality of bone screws, said seat surface defining a seat plane perpendicular to a reference plane containing one of said orthogonal axes, said seat surface having a plurality of raised surfaces for supporting the bone screws at preselected angles relative to said reference plane.

17. A fixator as set forth in claim 16 wherein said raised surfaces are formed on an alignment bracket removable from said one bone screw clamp.

18. A clamp assembly for a fixator comprising a flat interior seat surface for supporting a plurality of bone screws, said seat surface defining a seat plane and a plane of symmetry perpendicular to said seat plane, said seat surface having a plurality of complementary bosses symmetrically disposed relative to said plane of symmetry for supporting the bone screws in an orientation such that the longitudinal axis of each bone screw is contained in a plane parallel to said seat plane and has a preselected angle relative to said plane of symmetry.

19. A clamp assembly as set forth in claim 18 wherein said bosses each have a cross section in a plane parallel to said seat plane, each said cross section being triangular.

20. An alignment bracket for a clamp assembly of a fixator, said clamp assembly having a flat interior seat surface for supporting a plurality of bone screws, said seat surface defining a seat plane and a plane of symmetry perpendicular to said seat plane, said seat surface having a raised surface adapted for supporting said alignment bracket, said alignment bracket being adapted for keyed engagement with said seat surface to have a predetermined orientation relative to said plane of symmetry, said alignment bracket having a pair of complementary shoulders which, when said alignment bracket is in said keyed engagement with said seat surface, are symmetrically disposed relative to said plane of symmetry for supporting the bone screws in an orientation such that the longitudinal axis of each bone screw is contained in a plane parallel to said seat plane and has a preselected angle relative to said plane of symmetry.

21. An alignment bracket as set forth in claim 20, and further comprising an elongate bracket base having opposite which said shoulders are fixed.

22. An alignment bracket as set forth in claim 21, and further comprising a central bracket stem fixed to said bracket base, said bracket stem being adapted for keyed engagement with said seat surface.

\* \* \* \* \*